United States Patent [19]

Kolobov et al.

[11] Patent Number: 5,744,452
[45] Date of Patent: Apr. 28, 1998

[54] γ-L-GLUTAMYL CONTAINING IMMUNOMODULATOR COMPOUNDS AND METHODS THEREWITH

[75] Inventors: Alexander A. Kolobov, Sestroretsk; Andrey S. Simbirtsev, St.-Petersburg; Sergey V. Kulikov, St.-Petersburg; Alexey N. Prusakov, St. Petersburg; Natalia M. Kalinina, St. Petersburg; Natalia V. Pigareva, St. Petersburg; Alexander U. Kotov, St. Petersburg; Vladimir M. Shpen, St. Petersburg; Oleg A. Kaurov, St. Petersburg; Sergey A. Ketlinsky, St. Petersburg, all of Russian Federation

[73] Assignee: Edward T. Wei, Berkeley, Calif.

[21] Appl. No.: 634,718

[22] Filed: Apr. 18, 1996

[30] Foreign Application Priority Data

Nov. 29, 1995 [RU] Russian Federation ............ 95119704
Dec. 6, 1995 [RU] Russian Federation ............ 95120266

[51] Int. Cl.$^6$ ............ A61K 38/00; A61K 31/40; A61K 31/38; C07D 333/22
[52] U.S. Cl. ............ 514/19; 514/419; 514/438; 548/496; 549/76
[58] Field of Search ............ 548/496; 549/76; 514/419, 438, 19

[56] References Cited

U.S. PATENT DOCUMENTS

| | | | |
|---|---|---|---|
| 4,125,626 | 11/1978 | Orlowski et al. | 424/319 |
| 4,568,489 | 2/1986 | Floyd | 260/112.5 R |
| 4,758,551 | 7/1988 | Meister et al. | 514/18 |
| 5,206,220 | 4/1993 | Hilton | 514/19 |

FOREIGN PATENT DOCUMENTS

WO 9217191 10/1992 WIPO.
WO 9308815 5/1993 WIPO.

OTHER PUBLICATIONS

Christian, J.S., "A Review of the Pharmacology, Clinical Applications, and Toxicology of Thymopentin, " *Transgenica: The Journal of Clinical Biotechnology*, 1, pp. 23–34 (1994).

Prezioso et al., "γ–Glutamyltranspeptidase Expression Regulates the Growth–Inhibitory Activity of Anti–Tumor Prodrug γ–L–gultaminyl–4–hydroxy–3–iodobenzene," *Int. J. Cancer*, 56, pp. 874–879 (1994).

Li Kam Wa et al., "The Antinatriuretic Action of γ–L–glutamyl–5–hydroxy–L–tryptophan is Dependent on its Decarboxylation to 5–hydroxytryptamine in Normal Man," *Br. J. Clin. Pharmac.*, 387, pp. 265–269 (1994).

Illum, Lisbeth, "The Nasal Delivery of Peptides and Proteins," *Trends in Biotechnology*, 9, pp. 284–289 (1991).

Goldstein et al., "Thymopoietin to Thymopentin: Experimental Studies," *Thymopentin in Experimental and Clinical Medicine, Survey of Immunologic Research*, 4, Supp. 1, pp. 1–10 (1985).

Gillis et al., "T–Cell Growth Factor: Parameters of Production and Quantitative Assay for Activity," *J. Immunol.*, 120:6, pp. 2027–2032 (1978).

Hasegawa et al., Agric. Biol. Chem., vol. 42, No. 2, pp. 371–381, (1978).

Wellner, Methods in Onyymology, vol. 113, 1985 pp. 564–566.

Hirata, Bulletin of the Chemical Society of Japan, vol. 45, No. 6, 1972 pp. 1790–1794.

*Primary Examiner*—Deborah Lambkin
*Attorney, Agent, or Firm*—Majestic, Parsons, Siebert & Hsue

[57] ABSTRACT

The new class of synthetic immunomodulatory molecules having a γ-L-glutamyl- moiety at the amino terminus are provided as illustrated by Formula 1.

FORMULA 1

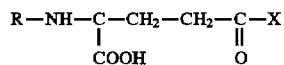

In Formula 1, the Greek symbols designate the noted carbon atoms, R is hydrogen, acyl or alkyl, and X is an aromatic or heterocyclic amino acid or its derivative. Included as members of the new class (in addition to Bestim, γ-L-glutamyl-L-tryptophan) are those compounds where R=hydrogen and X=L-tryptophan, such as γ-L-glutamyl-$N_{in}$-formyl-L-tryptophan, N-methyl-γ-L-glutamyl-L-tryptophan, N-acetyl-γ-L-glutamyl-L-tryptophan, and γ-L-glutamyl-β-thienyl-D-alanylamide. A preferred embodiment, termed "BESTIM," has the chemical structure of γ-L-glutamyl-L-tryptophan.

14 Claims, No Drawings

γ-L-GLUTAMYL CONTAINING IMMUNOMODULATOR COMPOUNDS AND METHODS THEREWITH

FIELD OF THE INVENTION

The invention generally relates to immunostimulant compounds, and more particularly relates to immunostimulant compounds including a γ-L-glutamyl moiety that stimulates maturation and differentiation of certain classes of white blood cells within the body. This selective stimulation of white blood cell differentiation and proliferation enhances the body's defenses against disease-causing organisms and also modulates and ameliorates self-inflammatory conditions.

BACKGROUND OF THE INVENTION

The immune system is a network of cells adapted to protect the organism against pathogens and cells that are not recognized as "self." Once the immune system is activated, it enlists the participation of a variety of cells and molecules to mount an effector function designed to eliminate the "non-self" entity within the body. Lymphocytes are cells of the immune system that are capable of specifically recognizing and selectively eliminating foreign entities. By contrast to other cells of the immune system, such as neutrophils which are considered non-specific in their reactions to invaders, the characteristics of lymphocytes confer specificity, diversity, memory and self/nonself recognition to the immune response.

There are two major populations of lymphocytes: B lymphocytes and T lymphocytes. B lymphocytes originate and mature within the bone marrow and are responsible for formation of antibody molecules. T lymphocytes also arise from the bone marrow but mature in the thymus. There are two major subpopulations of T-cells: T helper cells and T cytotoxic cells. The two types of T cells can be distinguished by the presence of one of two membrane glycoproteins, either CD4 or CD8. The T-helper cells (which express CD4) when activated by antigen-complexes (foreign molecules coupled to special proteins) respond by secreting various growth factors known collectively as cytokines. These cytokines are signals that activate other cells of the immune system, including the T-cytotoxic cells. The T-cytotoxic cells (which express CDS) when activated, proliferate and differentiate into cytotoxic T lymphocytes (CTL) which are able to monitor for and eliminate from the body pathogenic cells, foreign cells, virus-infected cells, and tumor cells.

The normal development, maturation and differentiation of T lymphocytes are regulated by peptide hormones secreted by thymic cells. One such hormone is the 49-amino acid residue peptide, thymopoietin. Residues 32–36 of thymopoietin, Arg-Lys-Asp-Val-Tyr, retain the biological activities of thymopoietin, and are the basis for an immunomodulatory drug called thymopentin. The therapeutic applications of thymopentin include use for rheumatoid arthritis, dermatologic conditions, infections by bacteria, virus and fungi, reversal of immune depression due to surgery or to cancer therapy, potentiation of responses to hepatitis B virus vaccination, and treatment of acquired immunodeficiency syndrome (AIDS), a condition in which T-helper (CD4) cells are specifically attacked by the virus (Christian, J. S., "A Review of the Pharmacology, Clinical Applications, and Toxicology of Thymopentin," *Transgenica: The Journal of Clinical Biotechnology*, 1, pp. 23–34, 1994).

A second compound with similar properties to thymopentin is the dipeptide, Glu-Trp, called thymogen. The sequence -Glu-Trp- also occurs in the molecule that is precursor for the synthesis of thymopoietin but -Glu-Trp- is not part of the 49-amino acid hormone nor is this dipeptide recognized as being a contributor to biological activity of thymopoietins. Thymogen was discovered and was used primarily in Russia for the prophylaxis and treatment of infections. Thymogen was used for the enhancement of immune function after damage of lymphocytes by accidental exposure to irradiation as a result of the Chernobyl incident. (Khavinson et al., WO 92/17191 and WO 93/08815, "Pharmaceutical Dipeptide Compositions and Methods of Use Thereof").

γ-L-Glutamyl derived peptides occur naturally in the body, the most well-known example being the tripeptide glutathione. Synthetic γ-L-glutamylmolecules have also been used as candidate drugs. These candidates are called "prodrugs" because the γ-L-glutamyl moiety is used as a carrier for the active portion of the molecule. For example, γ-L-glutaminyl-4-hydroxy-3-iodobenzene demonstrate antitumor activity in human and in mouse melanoma cell lines. It is thought that the anti-tumor activities of this compound is due to enzymatic release of 4-hydroxy-3-iodobenzene near the tumor cells (Prezioso et al., "γ-Glutamyltranspeptidase Expression Regulates the Growth Inhibitory Activity of the Anti-tumor Prodrug γ-glutaminyl-4-hydroxy-3-iodobenzene," *International Journal of Cancer*, 56, pp. 874–879, 1994). Also, γ-L-glutamyl-dopamine and γ-L-glutamyl-5-hydroxytryptophan have been described as prodrugs that might carry and supply dopamine and 5-hydroxy-tryptophan to brain neurons (Likamwa et al., "The Antinatriuretic Action of γ-L-glutamyl-5-hydroxy-L-tryptophan is Dependent on its Decarboxylation to 5-hydroxytroptamine in Normal Brain," *British Journal of Clinical Pharmacology*, 387:265–269, 1994).

SUMMARY OF THE INVENTION

"Bestim," an acronym of the coined phrase "best immunomodulator," is the name given to a preferred embodiment of a new class of compounds to which this invention pertains and which have immunomodulatory properties. The Bestim compound itself has the chemical structure of γ-L-glutamyl-L-tryptophan. The new class of synthetic immunomodulatory molecules have a γ-L-glutamyl- moiety at the amino terminus, as illustrated by Formula 1.

FORMULA 1

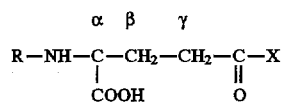

In Formula 1, the Greek symbols designate the respective carbon atoms in relation to the one carboxyl group (the γ carbon being adjacent to another carboxyl group), R is hydrogen, acyl or alkyl, and X is an aromatic or heterocyclic amino acid or its derivative. Included as members of the new class (in addition to Bestim, γ-L-glutamyl-L-tryptophan) are those compounds where R=hydrogen and X=L-tryptophan, such as γ-L-glutamyl-$N_{in}$-formyl-L-tryptophan, N-methyl-γ-L-glutamyl-L-tryptophan, N-acetyl-γ-L-glutamyl-L-tryptophan, and γ-L-glutamyl-β-thienyl-D-alanylamide.

The preferred embodiment Bestim has a potent immunostimulatory activity when tested in various experimental assay systems in vitro and in vivo. The mechanism of its biological action is related to the induction of differentiation of bone marrow T-lymphocyte precursors, stimulation of lymphocyte proliferation, and increase in production of various cytokines, including interleukin-2. The net result of Bestim's pharmacological effect is a selective increase in the number of T-helper lymphocytes, that is, cells that contain the CD4 marker.

Preclinical studies of Bestim demonstrate immunostimulatory activity at sub-nanomolar concentrations. In vivo it acts at doses of 10 ng to 1 μg per kg body weight and has no observable toxicity at doses 500 to over a million-fold higher than the immunostimulatory dose. In animal studies, it is active after oral administration.

In preliminary studies in humans, Bestim increased immune function as measured by laboratory changes of lymphocyte function. These laboratory changes were accompanied by positive indicators of benefit in clinical outcome.

A drug designated as an "immunodulatory drug" has a well-defined set of actions. Bestim is effective as a drug for immunotherapy of infectious diseases and for reinstatement of immune reactivity previously decreased by exposure to radiation or other stress factors such as cancer chemotherapy or surgery.

Thus, the Formula 1 compounds possessing immunomodulatory activity are usefully administered to patients to modify immunodeficiency caused by natural or drug-induced states, administered to patients to ameliorate and to reduce the risks infections from micro-organisms, especially administered to hospitalized patients, to burn victims, to patients undergoing surgery, to patients undergoing cancer chemotherapy, because such individuals are especially prone to infections. Further, the Formula 1 immunomodulatory compounds may be administered to patients with symptomatic or asymptomatic viral infections, in order to facilitate viral elimination and to enhance immune surveillance of pathogenic organisms and thus to reduce the likelihood of recurrence of disease, for example, for individuals who are sick from or are carriers of herpes viruses, varicella viruses, hepatitis viruses and HIV, administered to patients with diseases that alter natural cells so that they are recognized as "foreign" by the body, for example, in conditions such as cancer, and administered to patients with self-inflammatory (autoimmune) diseases such as rheumatoid arthritis, multiple sclerosis, scleroderma—in order to adjust the immune system to equilibrium.

In addition to these uses with patients at high risk of disease or expressing symptoms of disease, the Formula 1 immunomodulatory compounds may be administered to healthy populations in anticipation of epidemic infections, for example, in conjunction with influenza vaccinations, or to invigorate the immune response to pathogens in conjunction with vaccinations, for example, for vaccination against hepatitis—the technical term for this is the use of the invention as an "adjuvant" to vaccination.

These uses may be administered by dosages in the range of about 1 ng to about 1000 μg per kg of body weight, given as a single dose or intermittently over a period of up to a month or more, and the routes of delivery are preferably by parenteral injection, by oral or nasal inhalation, or by oral ingestion.

DETAILED DESCRIPTION OF THE PREFERRED EMBODIMENTS

Broadly, compounds of this invention are unique chemical substances that modulate the population of T-helper cells to optimum levels in the host. For example, modulation of the immune system to increase the number of T-helper cells increases the organism's ability to cope with infections from bacteria or viruses. A modulation to increase the number of T-helper cells also helps the body to fight against cancer cells that have become foreign to the host. Alternatively, these substances also enable the host to adjust to diseases arising from disarrangement of self-recognition processes in which there is excessive attack by host T-cells against endogenous tissues. In such instances, the inventive compounds modulate the T-cell population so that the signs and symptoms of self-directed inflammatory (autoimmune) diseases such as rheumatoid arthritis and multiple sclerosis are ameliorated.

"Bestim," an acronym of the coined phrase "best immunomodulator," is the name given to a preferred embodiment of a new class of compounds to which this invention pertains and which have immunomodulatory properties. The Bestim compound itself has the chemical structure of γ-L-glutamyl-L-tryptophan. The new class of synthetic immunomodulatory molecules have a γ-L-glutamyl- moiety at the amino terminus, as illustrated by Formula 1.

FORMULA 1

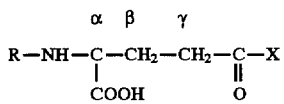

In Formula 1, The Greek symbols designate the respective carbon atoms in relation to the carboxyl group, R is hydrogen, acyl or alkyl, and X is an aromatic or heterocyclic amino acid or its derivative. Included as members of the new class (in addition to Bestim, γ-L-glutamyl-L-tryptophan) are those compounds where R=hydrogen and X=L-tryptophan, such as γ-L-glutamyl-$N_{in}$-formyl-L-tryptophan, N-methyl-γ-L-glutamyl-L-tryptophan, N-acetyl-γ-L-glutamyl-L-tryptophan, and γ-L-glutamyl-β-thienyl-D-alanylamide.

Appropriate derivatives of aromatic or heterocyclic amino acids for "X" are: amides, mono- or di-($C_1$–$C_6$) alkyl substituted amides, arylalmides, and ($C_1$–$C_6$) alkyl or aryl esters. Further, appropriate acyl or alkyl moieties for "R" are: branched or unbranched alkyl groups of 1 to 6 carbons, acyl groups from 2 to 10 carbon atoms, carbobenzyloxy, and t-butyloxycarbonyl.

A. Bestim: Biological Activity in Vitro

1. Comparison of Bestim and Thymogen on Murine Bone Marrow Lymphocyte Differentiation Differentiation of murine T-lymphocyte precursors was studied by the enumeration of cells expressing early surface differentiation marker Θ-antigen. Bone marrow cells were obtained from CBA strain mice killed by cervical dislocation. Cells were washed from femur bones with Hank's balanced salt solution and washed 3 times with RPM 1-1640 medium by centrifugation at 400 xg. Peptides at desired concentrations were incubated with $1 \times 10^6$/ml of obtained cells for 1 hour at 37° C. Theta-antigen ("Θ-antigen") expression has been determined with antibrain antibodies in a cytotoxicity assay using complement-dependent cell lysis (Terasaki et al., "Microdroplet Lymphocyte Cytotoxicity Test. Manual of Tissue Typing Techniques," National Institutes of Health, Bethesda, Md., pp 50–55, 1972). Dead cells were counted microscopically after eosin staining. According to the data represented in Table 1 Bestim induced dose-dependent T-Lymphocyte differentiation in culture at doses from 1 ng/ml to 100 μg/ml. Its activity was much stronger than that of the reference thymogen peptide. Analysis of the dose-response data indicated that Bestim was at least 500-fold more potent than thymogen.

TABLE 1

Changes in Θ-antigen expression on murine bone marrow cells in the presence of Bestim or thymogen.

| Peptides μg/ml | Bestim | Thymogen |
|---|---|---|
| 0 | 10 ± 1.8 | |
| 0.0001 | 14 ± 1.5 | 10 ± 0.5 |
| 0.001 | 29 ± 2.4* | 10 ± 1.2 |
| 0.01 | 30 ± 2.8* | 10 ± 0.5 |
| 0.1 | 34 ± 1.9* | 9 ± 1.0 |
| 1.0 | 49 ± 1.2* | 21 ± 0.8* |
| 10 | 48 ± 0.8* | 36 ± 2.8* |
| 100 | 47 ± 1.0* | 37 ± 2.2 |

*p < 0.05, compared to control values

2. Comparison of Bestim and Thymogen on Interleukin-2(IL-2) Production

Spleen cells from CBA mice were cultured in tissue culture plates at a $10^6$ cells/ml in RPMI-1640 medium supplemented with 10% fetal calf serum, 2 mM L-glutamine, and 80 μg/ml of Gentamycin. 1 μg/ml of Concanavalin A was used to activate basal IL-2 production from murine spleen lymphocytes. Bestim was added to cell cultures at the "0" time. After 36 hours supernatants were collected, centrifuged at 800 xg and IL-2 levels were measured in a CTLL-2 cell assay (Gillis et al., "T-cell Growth Factor: Parameters of Production and Quantitative Assay for Activity," *J. Immunol.*, 120: 2027–2032, 1978). Results are shown in Table 2. It can be seen that Bestim enhances IL-2 secretion from cells at low doses. However, due to the variations in the method for IL-2 measurements clear dose-response comparisons could not be achieved.

TABLE 2

Effect of Bestim and Thymogen on IL-2 production by murine spleen cells.

| Peptides μg/ml | Bestim | Thymogen |
|---|---|---|
| 0 | 71 ± 4 | |
| 0.001 | 159 ± 13* | 114 ± 12* |
| 0.01 | 134 ± 8* | 106 ± 10* |
| 0.1 | 98 ± 5* | 106 ± 5* |
| 1.0 | 157 ± 10* | 189 ± 13* |
| 10 | 95 ± 4* | 80 ± 9 |
| 100 | 112 ± 3* | 89 ± 3 |

*p < 0.05, compared to control values

B. Bestim Activity: in vivo studies

Effect of Bestim on Murine Thymocyte Differentiation

Bestim was injected into 3-month old CBA mice at doses ranging from 10 ng/kg to 100 μg/kg intraperitoneally. Mice were killed by cervical dislocation 24 hours after injection, the thymus gland removed, and the cells isolated by centrifugation and washed in RPMI-1640 medium. Expression of surface differentiation antigens were measured using monoclonal antibodies to L3T4 (T-helper marker), Lyt 2 (T-cytotoxic marker) and Thy-1 (common T-lymphocyte marker) molecules in a cytotoxicity assay using complement-dependent cell lysis (Terasaki et al., 1972). Dead cells were counted microscopically after eosin staining. The results are summarized in Table 3.

TABLE 3

Effect of Bestim on the murine thymocyte differentiation.

| Bestim μg/kg i.p. | Percent of thymocytes expressing cell surface markers | | |
|---|---|---|---|
| | L3T4 | Lyt2 | Thy-1 |
| 0 | 43 ± 2 | 50 ± 5 | 90 ± 2 |
| 0.01 | 40 ± 8 | 45 ± 5 | 95 ± 3 |
| 0.1 | 55 ± 1* | 44 ± 2 | 89 ± 2 |
| 1 | 54 ± 1* | 46 ± 1 | 91 ± 1 |
| 10 | 64 ± 1* | 47 ± 2 | 90 ± 1 |
| 100 | 70 ± 1* | 48 ± 1 | 91 ± 0 |

*p < 0.05, compared to controls

These data show that Bestim preferentially induces differentiation of a subset of T-helper lymphocytes in murine thymus.

The potent activity of Bestim in these tests suggested that some of the drug may be able to get through the gastrointestinal absorption barriers to exert pharmacological effects in vivo. Bestim dissolved in saline was given orally, for 5 days, to groups of 5 mice per dose. After 30 days, the quantity of Θ-antigen positive cells in bone marrow and IL-2 production by splenocytes were measured (as described in later in methods). The data are shown in Table 4.

TABLE 4

Pharmacological activity of Bestim after oral administration to mice.

| Bestim, oral administration μg/kg/day for 5 days | Θ-antigen expression % of cells | IL-2 production Units/ml |
|---|---|---|
| 0 (control) | 19 ± 1.9 | 36 ± 3.4 |
| 0.1 | 48 ± 1.9* | 43 ± 11.5 |
| 1 | 48 ± 3.0* | 73 ± 16.3 |
| 10 | 36 ± 2.3* | 130 ± 11.8* |

*P < 0.05, compared with control

C. Bestim: Pharmacokinetic Properties and the Absence of Toxicity

As earlier described, efforts have previously been made to prepare "prodrug" candidates where the γ-L-glutamyl moiety is used as a carrier for the active portion of the molecule. Thus, the design of the prodrug candidates has incorporated the γ-L-glutamyl moiety to stabilize and protect the molecule from degradation. The carrier-active moiety combination is then delivered to the target site where γ-L-glutamyltranspeptidases hydrolyze γ-L-glutamic acid from the prodrug and release the active molecule. The γ-L-glutamyl portion of Bestim is, however, considered to be intrinsic to the bioactivity of the entire molecule because tryptophan alone has little immunomodulatory activities.

The presence of the γ-L-glutamyl moiety in Bestim (and other of the Formula 1 inventive compounds) confers two important properties: resistance to degradation by aminopeptidases and increased potency. Aminopeptidases are ubiquitous enzymes that attack and hydrolyze peptide bonds (carboxylamide bonds) adjacent to α-carbons containing a free amino group. Aminopeptidases are not active against Bestim. The aminopeptidases limit the duration of action of peptides which normally contain the amino function on the α-carbon. For example, the immunomodulatory pentapeptide called thymopentin, Arg-Lys-Asp-Val-Tyr, breaks down in plasma with a half-life of 30 seconds and it would be expected that Glu-Trp (thymogen) would share a similar fate. The rapid breakdown of thymopentin requires that single doses of 50 mg be injected parenterally three times a week to achieve therapeutic effect. By contrast, the presence of the γ-L-glutamyl moiety on Bestim confers resistance to degradation by aminopeptidases and prolongs duration of action, hence the therapeutic doses are much smaller than the 50 mg required for thymopentin.

Dose-response analysis of the data shown in Table 1 showed that Bestim is at least 500 times more potent than thymogen. The increased potency resulting from the γ-L-glutamyl configuration has important implications for the practical problems of drug delivery to receptors. Parenteral administration of drugs to patients, by the intravenous, intramuscular or subcutaneous routes, is generally inconvenient because it requires specially formulated drugs, needles and syringes, and trained personnel or a trained patient for injection. Thus, in clinical trials of new parenterally-administered drugs, the ability to select a precise dosage regimen that optimize the drug response is an expensive trial and error procedure. A potent drug, such as Bestim, with a molecular weight of 333 Daltons, can easily be delivered by the nasal route, using spray or drops, or by the inhalation route, using nebulizers and aerosols, to achieve therapeutic effect. For example, the 1-2% absorption obtained by nasal absorption of small molecules would be sufficient to deliver a therapeutic dose, without recourse to enhancers of absorption such as bile salts, surfactants or carriers (Illum, "The Nasal Delivery of Peptides and Proteins," *Trends in Biotechnology*, 9, pp. 284-289, 1991). The enhancers are frequently irritating and not acceptable for repeated administrations of drugs. It is expected that the nasal or inhalation routes of delivery, or oral administration, of Bestim would permit a wide range of clinical applications.

The innovative replacement of L-glutamic acid with the γ-L-glutamic acid substitution enhances potency but this gain in potency does not affect another desirable characteristic of Bestim relative to thymogen: namely, an absence of toxicity. The absence of toxicity is obtained because the breakdown products of Bestim, derived from enzymes such as γ-L-glutamyl-transpeptidase and γ-L-glutamylcysteinsynthetase that hydrolyse Bestim, yield endogenous the amino acids, glutamic acid and tryptophan, which are non-toxic at therapeutic doses of Bestim.

To illustrate this point and in preparation for clinical studies, acute and sub-acute toxicity studies were conducted in animals with Bestim according to conditions of good-laboratory practices. Bestim, prepared as a sterile lyophitized powder in ampoules, was dissolved in sterile 0.9% NaCl solution and injected intramuscularly in all experiments.

Acute toxicity: Rodents (mice and rats) and dogs were randomized into groups of equal numbers of males and females. Animals were inspected daily for 14 days after a single dose of Bestim (intramuscular):

mice—5000.0 mg/kg rats—500.0 mg/kg dogs—500.0 mg/kg

Body weight, overall appearance and behavior were evaluated each day and, at the end of two weeks, macroscopic and histopathological examinations of the internal organs (heart, lungs, pleural and peritoneal cavities, muscles, stomach, small and large intestine, liver, spleen, pancreas, kidneys, bladder, thyroid, brain, skin and testes/ovaries) of all animals were conducted.

No deaths were observed in any of the animals tested and the recorded parameters of general appearance, behavior, body weight, hematological, biochemical and physiological indices, and macroscopic and histopathological examination of internal organs were all within normal limits.

Subacute Toxicity Studies: In a second set of experiments, Bestim was administered for longer durations, accordingly:

rats: 1 mg/kg and 100 mg/kg, administered intramuscularly daily for 3 months and for 6 months dogs: 1 mg/kg, 10 mg/kg and 100 mg/kg, administered intramuscularly daily for 1 month and for 3 months.

Repeated injection of Bestim in rats did not cause death in any animal, or produce changes in behavior, or in hematological, biochemical, or physiological parameters. The morphological appearance of all organs at the macroscopic and histological levels were normal. Both doses in rats induced a slight increase in body weight in experimental animals.

Repeated injection of Bestim in dogs did not cause death in any animal, or produce changes in behavior, body weight, hematological, biochemical or physiological parameters. Macroscopic and histological examination of all examined organs showed no significant changes. There were no local inflammatory reactions at the site of injection.

In conclusion, these toxicity tests showed that Bestim is free of acute or subacute toxic properties in rodents and dogs. The tested doses relative to the expected doses for therapeutic trials were on the order of 5,000,000-fold for single administration and 100-fold for repeated administration. The Bestim preparations were then evaluated in the clinic.

EXAMPLE 1

Inventive Embodiments

A: γ-L-glutamyl-L-tryptophan

B: N-methyl-γ-L-glutamyl-L-tryptophan

C: N-acetyl-γ-L-glutamyl-L-tryptophan

D: γ-L-glutamyl-$N_{in}$-formyl-L-tryptophan

E: γ-L-glutamyl-β-thienyl-D-alanyl-amide

Comparison peptide: L-glutamyl-L-tryptophan (thymogen)

The data in Table 5 and Table 6 show that the immunostimulatory actions of γ-L-glutamyl substituted dipeptides are not unique to Bestim only (A), but are also obtained by other modifications of the γ-L-glutamyl-L-tryptophan dipeptide. For example, active compounds were obtained by substitution on the amino-terminus with methyl or acetyl groups resulted (B and C), modification of the nitrogen of the indole nucleus of tryptophan ($N_{in}$-formyl substitution, compound D) or by replacement of the tryptophan residue with another aromatic amino acid residue (β-thienyl-D-alanine, compound E). However, none of the modified compounds were as active as Bestim in bioassays for activity.

It should be noted, however, that there is molecular specificity of the receptors mediating the Bestim effect as similar molecules of the following structures: γ-L-glutamyl-L-proline, γ-L-glutamyl-L-phenylalanine, γ-L-glutamyl-L-tyrosine, γ-L-glutamyl-L-histidine, γ-L-glutamyl-L-leucine, and γ-L-glutamyl-L-isoleucine, had little, if any, of the activities of Bestim in the in vitro assays used.

TABLE 5

Percent of murine bone marrow cells expressing
(Θ-antigen in the presence of Bestim, its analogs and thymogen

| Peptides (µg/ml) | Bestim A | B | C | D | E | Thymogen |
|---|---|---|---|---|---|---|
| 0 | 10 | 10 | 10 | 10 | 10 | 10 |
| 0.0001 | 25* | 20* | 19 | 24* | 20* | — |
| 0.001 | 31* | 29* | 28* | 25* | 23* | — |
| 0.01 | 35* | 34* | 35* | 30* | 20* | 18 |
| 0.1 | 37* | 40* | 40* | 36* | 27* | 20* |
| 1.0 | 49* | 47* | 45* | 42* | 28* | 25* |
| 10 | 52* | 51* | 46* | 48* | 36* | 29* |
| 100 | 60* | 53* | 50* | 53* | 40* | 32* |

*P < 0.05, compared with controls

TABLE 6

Effect of Bestim, its analogs and thymogen on
interleukin-2 production by murine spleen cells.

| Peptides (µg/ml) | Bestim A | B | C | D | E | Thymogen |
|---|---|---|---|---|---|---|
| 0 | 123 ± 10 | 123 ± 10 | 123 ± 10 | 123 ± 10 | 123 ± 10 | 123 ± 10 |
| 0.001 | 149 ± 2* | 134 ± 6 | 128 ± 7 | 114 ± 16 | 146 ± 28 | 115 ± 8 |
| 0.01 | 162 ± 4* | 147 ± 8 | 136 ± 7 | 125 ± 3 | 127 ± 26 | 132 ± 16 |
| 0.1 | 172 ± 9* | 152 ± 7 | 149 ± 5 | 153 ± 20 | 128 ± 10 | 118 ± 11 |
| 1.0 | 271 ± 11* | 165 ± 6* | 157 ± 9* | 132 ± 8 | 156 ± 11* | 128 ± 5 |
| 10 | 160 ± 8* | 171 ± 6* | 170 ± 4* | 144 ± 7 | 172 ± 12* | 129 ± 10 |
| 100 | 186 ± 6* | 180 ± 11* | 174 ± 8* | 154 ± 5* | 198 ± 7* | 136 ± 4* |

*P < 0.05, compared with controls

Example of solution synthesis of H-γ-L-Glu-L-Trp—OH (Bestim)

Boc-L-Glu-OBzl (0.6 g, 0.0018 mol) is dissolved in dimethylformamide (DMF) (2 ml) and hydroxysuccinimide (HOSu) (0.2 g, 0.0018 mol) is added. Mixture is cooled to 5° C. below zero under intensive stirring and dicyclohexylcarbodiimide (CDI) (0.37 g, 0.0018 mol) is added.

The reaction mixture is stirred at 0° C. for an hour and at the room temperature for 12 hours. Precipitated dicyclohexylurea is filtrated and the hydrochloride salt of H-L-Trp-OBzl (0.72 g, 0.0022 mol) and triethylamine (TEA) (0.3 ml, 0.0023 mol) are added. The mixture is stirred at room temperature for 16 hours. The solution is filtrated, diluted up to 50 ml with water and extracted with ethylacetate (3×40 ml). The final organic solution is washed successively with water (20 ml), 2N $H_2SO_4$ (2×20 ml), saturated solution of $Na_2SO_4$ (2×20 ml) and dried over anhydrous $Na_2SO_4$. Ethylacetate is removed in vacuo and trifluoroacetic acetic acid (TFA) (16 ml, 50% solution in $CH_2Cl_2$) is added. The mixture is stirred at room temperature for 45 minutes and evaporated in vacuo. The residual oil of TFA. H-γ-L-Glu-L-Trp-OBzl is dried over sodium hydroxide in a dessicator.

TFA.H-γ-L-Glu-L-Trp-OBzl (0.3 g, 0.00048 mol) is dissolved in isopropyl alcohol (25 ml) and $NaHCO_3$ (0.16 g, 0.00096 mol) and $HCOONH_4$ (0.18 g, 0.0024 mol) are added. The reaction mixture is warmed up to 50° C. and 10% palladium catalyst (250 mg) suspended in $H_2O$ (25 ml) is added under intensive stirring. In 30 minutes, the palladium catalyst is filtered out, isopropyl alcohol is removed in vacuo and the residual water solution is lyophilized to yield Bestim, H-γ-L-Glu-L-Trp—OH.

Example of solid-phase synthesis of H-γ-L-Glu-L-$N_{in}$-formyl-Trp—OH

The desired molecule was synthesized using 1% divinylbenzene cross-linked polystyrene as solid support. 0.6 g of Nα-tertBoc-$N_{in}$-formyl-L-tryptophan-Merrifield resin (content of Trp 0.5 mmol/g resin) is placed into reaction vessel. The program of automated synthesis is as follows (see schedule below).

Schedule for Peptide Synthesis

| Step | Reagent | No. Repeats | Vol (ml) | Time (min) |
|---|---|---|---|---|
| 1 | 50% TFA in $CH_2Cl_2$ | 2 | 5 | 2 + 30 |
| 2 | $CH_2Cl_2$ | 6 | 8 | 2 |
| 3 | 5% DIEA in $CH_2Cl_2$ | 3 | 5 | 2 |
| 4 | $CH_2Cl_2$ | 6 | 8 | 2 |
| 5 | coupling* | 1 | 4 | 120 |
| 6 | DMAA | 2 | 8 | 2 |
| 7 | 2-propanol | 2 | 8 | 2 |
| 8 | $CH_2Cl_2$ | 2 | 8 | 1 |
| 9 | Ninhydrin test** | — | — | — |

TFA—trifluoroacetic acid, DIEA—diisopropylethylamine, DMAA—dimethylacetamide.
*coupling was carried out by active ester of 1-hydroxybenzotriazole (HOBt) which was prepared from three equivalents of Boc-L-Glu-α-OBzl, HOBt and dicyclohexylcarbodiimide (DCI) in DMAA for 30 minutes on ice.
**completion of coupling was verified by the Kaiser ninhydrin test (Kaiser et al., Anal. Biochem., 34:595, 1970). Incomplete coupling was repeated once more time.

Peptide was deprotected and cleaved from polymer with liquid hydrogen fluoride (HF) containing anisole and 10% m-cresol at 0° C. for 60 minutes. HF was removed in vacuo at 0° C, peptide was extracted with aqueous acetic acid, precipitated with ethyl ether, lyophilized and after deformylation with 0.2N sodium hydroxide was purified by preparative high-performance liquid chromatography (HPLC).

All Bestim analogs were synthesized according to the same scheme as in the schedule above, the use of different Boc-derivatives at the stage 5 being the only difference.

Verification of Synthesis

For example, Bestim was characterized by:
1. High-Performance Liquid Chromatography (HPLC), using a Chromatograph Gilson (France), eluent 0.1% TFA/acetonitrile, gradient 10–40%, 14 min run, column Delta-Pack C-18, 300 Å, 5 µm, 3.9×150 mm. The retention time of the product was 8.1 min and its purity, measured as the integrated area under the HPLC peak was 99.7%.

2. Amino acid analysis: using a LKB Amino acid analyzer Alpha Plus 4151 the product was hydrolyzed in 4N methansulfonic acid, containing 0.2% of tryptamine in vacuo, at 115° C., 24 hours. The peptide content of glutamic acid 1.0, tryptophan 0,94, confirming the presence of the desired residues.
3. Thin-layer chromatography (TLC): system I—n-butanol:ethylacetate:acetic acid:water=1:1:1:1, Rf=0.72; system 2 - sec-butanol:acetic acid:toluene:water=6:1:2:1, Rf=0.4.
4. Nuclear magnetic resonance spectrometry (NMR): NMR spectrometer Bruker GXP-300 equipped with Aspect 200 computer. In carbon NMR spectrum of the peptide (0.001 M/l solution) were detected: for Glu—at 30.0; 31.0; 57.2; 176.6; 178.3 ppm; for Trp—at 35.7; 58.3; 113.1; 116.6; 123.4; 124.3; 126.6; 129.0; 131.0; 140.3; 179.4 ppm.
5. Fast atom bombardment mass spectrometry (FAB-MS), molecular ion: calculated, 334.13 Da; found 333.73.

1. Study of Bestim Influence on the Murine Bone Marrow Lymphocyte Differentiation Differentiation of murine T-lymphocyte precursors was studied by the enumeration of cells expressing early surface differentiation marker—Θ-antigen which is an analog of the Thy-1 lymphocyte differentiation antigen. Bone marrow cells were obtained from CBA strain mice killed by cervical dislocation. Cells were washed from femur bones with Hank's balanced salt solution and washed 3 times with RPMI-1640 medium by centrifugation at 400 xg. Peptides at desired concentrations were incubated with $1 \times 10^6$/ml of obtained cells for 1 hour at 37° C. Θ-antigen expression were determined with antibrain antibodies in a cytotoxicity assay using complement-dependent cell lysis (Terasaki et al., 1972). Dead cells were counted microscopically after eosin staining untreated bone marrow cells served as a negative control, and murine thymocytes as a positive control.

2. Stimulation of Interleukin-2(IL-2) Production by Bestim

IL-2 production studies have been performed using murine spleen lymphocytes activated with Concanavalin A. Spleen cells from CBA mice were cultured in a tissue culture plates at a $1 \times 10^6$/ml concentration in RPMI-1640 medium supplemented with 10% fetal calf serum, 2 mM L-glutamine, 80 µg/ml Gentamycin and 1 µg/ml Concanavalin A as an inducer of basal level IL-2 synthesis. Bestim at various concentration was added to cell cultures at the "0" time. After 36 hours supernatants were collected, centrifuged at 800 xg and used for IL-2 levels determination in a CTLL-2 cell assay (Gillis et al., 1978). IL-2-dependent CTLL-2 cells were grown in RPMI-1640 medium in the presence of 1–2 U/ml recombinant IL-2 as a growth factor. Before assay, cells were washed twice to remove IL-2 from the medium. After this wash tested supernatants were added and cells were incubated for 36 hours. IL-2-induced proliferation was assayed using a $^3$H-thymidine incorporation method.

EXAMPLE 2

Goldstein and Audhya ("Thymopoietin to Thymopentin: Experimental Studies" in Thymopentin in Experimental and Clinical Medicine, Surv. Immunol. Res., 4, pp. 1–10, 1985) introduced the concept that immunomodulatory drugs act to restore immune imbalances, whether the imbalances are in the hyporesponsive or hyperresponsive state. The bi-directional activity of these drugs occur because of the nature of bioregulation in which imbalances are restored to an equilibrium set-point. In the case of hyporesponsiveness, administration of hormones that regulate T-lymphocytes acts to optimize and up-regulate the function of the self-defense system so that non-self organisms are more easily rejected. In the case of hyperresponsiveness, the administration of immunomodulatory drugs appears to dampen autoimmune processes in which the mistaken attack of useful "self" entities is now diminished. The categories of clinical applications of Bestim in hyporesponsive and hyperresponsive immune states are discussed and examples delineated.

Hyporesponsiveness or Immunodeficient Conditions

Immunodeficiency states fall into three general etiologic categories. First, there is immunosuppression that occurs as a consequence of disease processes. Second, there are immunodeficiencies that arise because of therapy for other diseases, so-called iatrogenic immunodeficiencies. Third, immunodificiencies may result from direct attack of T-lymphocytes by the human immunodeficiency virus (HIV) that causes the acquired immunodeficiency syndrome (AIDS).

Common disease processes that lead to immunodeficiency are malnutrition, neoplasias, aging, and infections. Malnourished people, patients with advanced widespread cancers and people with debilitating illnesses become sick and die more often because impaired cell-mediated and humoral immune responses increase susceptibility to infections by a variety of organisms. A state of generalized deficiency in immune responses is called anergy. Various types of infections, especially viral infections, lead to immunosuppression. A drug such as Bestim, capable of making the T-helper lymphocyte components of the immune system more robust, will be an important therapeutic agent for increasing the resistance of the patient to infections. For example, Bestim or its analogs, may be:

administered to patients, especially older patients, before or just after admissions to hospitals in order to reduce the risks of nosocomial (hospital-induced) infections, a common and severe clinical problem administered to burn victims, because such individuals are especially prone to infections administered to patients in anticipation of epidemic infections, for example, in conjunction with influenza vaccinations or hepatitis vaccinations, to invigorate the immune response to pathogens administered to patients with asymptomatic viral infections, in order to enhance immune surveillance of pathogenic organisms and reduce the likelihood of recurrence of disease, for example, for individuals who are carriers of herpes viruses, varicella viruses, hepatitis viruses and HIV.

Iatrogenic immunosuppression is most often due to drug therapies which either kill or functionally inactivate lymphocytes. Various chemotherapeutic drugs are administered to cancer patients, and these drugs are usually cytotoxic to both mature and developing lymphocytes as well as to granulocyte and monocyte precursors. Thus, cancer chemotherapy is almost always accompanied by a period of immunosuppression and increased risk of infections. Radiation treatment of cancer carries the same risks. Medications (granulocyte-colony stimulating factor) exist for increasing neutrophils in blood to combat infections that occur after cancer chemotherapy, but no medications are currently used for restoring lymphocytic functions. Major surgery, for example repair of aneurysms or by-pass operations, also decrease immune function in humans. The reasons for the decline in blood lymphocytes that occur because of major surgery are not clear, but an agent that elevates lymphocyte functions in such patients have therapeutic value in decreasing the likelihood of infections.

One final form of acquired immunosuppression that should be mentioned results from the absence of a spleen, caused by surgical removal of the organ after trauma or for the treatment of certain hematologic diseases or as a result of infarction in sickle cell disease. Patients without spleens are more susceptible to infections by some organisms, particularly encapsulated bacteria such as *Streptococcus pneumoniae*. The spleen is apparently required for the induction of protective humoral immune responses to such organisms. Bestim would help individuals without a spleen or without a thymus in resistance against infection by micro-organisms.

Results from Studies of Bestim in Humans

Preliminary studies were conducted to characterize the immunomodulatory properties of Bestim in human subjects. The protocol for the human subjects studies were reviewed and approved by a Hospital Committee (Moscow Hospital N-24) and informed consent was obtained from all subjects. All 62 patients received by intramuscular injection 0.1 mg of Bestim dissolved in 1.5 to 2.0 ml of sterile saline, one injection per day for 5 days. Patients participating in the clinical trials were from 2 groups:

The first group consisted of 34 patients with disseminated cancer (29 with colon cancer, 2 with primary brain gliomas, 2 with stage III gastric cancer, 1 with stage IIIb breast cancer). These patients received Bestim therapy after standard anticancer therapy which included surgical treatment and chemotherapy with 5-fluorouracil. It should be noted here that the goal of Bestim therapy in these patients was not to treat the tumor but to correct the immunodeficiency that accompanied this disease and which occurs as a consequence of anticancer therapy. Placebo (saline injections) were administered to 14 subjects.

The second group consisted of 28 patients with generalized surgical infection. Bestim was given together with standard antibiotic therapy.

Results

No detectable side-effects could be attributed to the administration of Bestim. Body temperature and blood pressure remained normal after Bestim and there were no complaints of headache or nausea, or evidence of allergic reactions. Hematological and biochemical parameters were within normal ranges and there was no local inflammatory reaction at the site of injection.

In the first group of patients with neoplasia, 30 out of the 34 patients (88%) subjectively felt better after Bestim therapy and according to the physician's opinion their conditions were improved. These opinions were based on the laboratory analysis data, physical examination of the patient, charts of body temperature changes, decreased evidence of infections, and increased appetite for food. A similar degree of improvement was observed in 4 of 14 patients (29%) receiving placebo injections. These differences between placebo and Bestim are statistically significant (Table 7).

Laboratory measurements (data in Table 8 to 10) were performed one day before and compared to values obtained three days after injection of Bestim. Of the 34 cancer patients, positive changes in immunological parameters were seen in 25 patients (73%), statistically insignificant in 6 patients (18%), and negative changes in 3 patients (9%). In the 14 saline-treated (placebo) group, four patients (29%) showed no changes in immunological indices and 10 of 14 patients (71%) exhibited negative changes in immunological parameters, as caused by the use of chemotherapy.

TABLE 7

Summary of Results on Cancer Patients

| | Placebo (N = 14, %) | Bestim (N = 34, %) |
|---|---|---|
| Positive | 0 | 73 |
| No significant change | 29 | 18 |
| Negative | 71 | 9 |

In the second group of patients with surgical infection, Bestim therapy combined with conventional methods resulted in more rapid clinical improvement and decreased the duration of the patient's stay in the clinic (Table 9).

TABLE 8

Changes in immunological parameters in cancer patients undergoing Bestim therapy

| Indices of Immune Function | Placebo Before | Placebo After | Bestim Before | Bestim After |
|---|---|---|---|---|
| CD3 (%) | 68 ± 13 | 49 ± 3* | 65 ± 4 | 70 ± 4# |
| CD3 (min/L) | 1518 ± 219 | 959 ± 112* | 1432 ± 183 | 1937 ± 234# |
| CD4 (%) | 31 ± 2 | 23 ± 2# | 28 ± 2 | 35 ± 2*# |
| CD4 (min/L) | 630 ± 46 | 430 ± 64*# | 582 ± 54 | 923 ± 114*# |
| CD8 (%) | 26 ± 1 | 24 ± 2 | 25 ± 2 | 29 ± 2 |
| CD8 (min/L) | 565 ± 50 | 420 ± 38*# | 572 ± 53 | 757 ± 75 |
| CD4/CD8 | 1.11 ± 0.01 | 0.98 ± 0.08# | 1.04 ± 0.08 | 1.16 ± 0.09*# |
| B-cells (%) | 5.2 ± 2.1 | 6.1 ± 1.9 | 5.0 ± 1.3 | 7.1 ± 2.2 |
| B-cells (min/L) | 215 ± 61 | 231 ± 66 | 152 ± 58 | 240 ± 90 |
| NK-cells (%) | 12.5 ± 2.1 | 8.2 ± 0.9# | 13.4 ± 2.3 | 12.0 ± 1.7 |
| NK-cells (min/L) | 268 ± 33 | 178 ± 33*# | 256 ± 44 | 267 ± 32 |
| IgG (g/L) | 12.5 ± 1.4 | 13.2 ± 1.3 | 14.2 ± 1.0 | 14.4 ± 1.0 |
| IgA (g/L) | 3.6 ± 0.5 | 3.0 ± 0.8 | 4.5 ± 0.8 | 4.1 ± 0.7 |
| IgM (g/L) | 1.6 ± 0.6 | 1.4 ± 0.9 | 1.9 ± 0.4 | 2.2 ± 0.4 |
| Blastransformation, spontaneous | 489 ± 96 | 363 ± 151 | 373 ± 63 | 434 ± 73 |
| Blastransformation, PHA | 6458 ± 1487 | 3257 ± 1875 | 5998 ± 1745 | 21661 ± 5674*# |
| Stimulation index, PHA | 16.4 ± 5.2 | 9.5 ± 2.3# | 15.9 ± 4.5 | 48.9 ± 10.3*# |
| Blastransformation, LPS | 2220 ± 588 | 959 ± 351# | 2328 ± 438 | 2738 ± 305 |
| Stimulation index, LPS | 6.0 ± 1.1 | 3.0 ± 0.8 | 7.6 ± 0.6 | 7.4 ± 0.7 |
| Chemiluminescence, luminol (spontaneous) | 590 ± 120 | 357 ± 194 | 475 ± 141 | 827 ± 299 |

TABLE 8-continued

Changes in immunological parameters in cancer patients undergoing Bestim therapy

| Indices of Immune Function | Placebo Before | Placebo After | Bestim Before | Bestim After |
|---|---|---|---|---|
| Chemiluminescence, luminol (induced) | 5997 ± 987 | 2548 ± 569* | 6991 ± 2101 | 5294 ± 789# |
| NK activity (%) | 30.1 ± 2.8 | 15 ± 5.1*# | 29 ± 1.3 | 28 ± 1.5# |
| Adhesion (%) | 47.5 ± 4.5 | 31.1 ± 2.8*# | 49.6 ± 5.9 | 47.6 ± 5.7# |
| NBT reduction test (Units) | 145 ± 15 | 115 ± 12# | 157 ± 19 | 160 ± 21# |
| Cationic proteins (Units) | 56.6 ± 6.1 | 44.1 ± 5.2# | 49.9 ± 5.9 | 52.4 ± 3.3# |
| Myeloperoxidase activity (Units) | 459 ± 96 | 347 ± 75 | 467 ± 87 | 479 ± 97 |

*difference among groups statistically significant, $P < 0.05$
difference between groups statistically significant, $P < 0.05$

TABLE 9

Changes in immunological parameters in patients with surgical infection undergoing Bestim therapy

| | Placebo Before | Placebo After | Bestim Before | Bestim After |
|---|---|---|---|---|
| CD3 (%) | 44 ± 4 | 45 ± 4 | 35 ± 5 | 65 ± 5* |
| CD4 (%) | 31 ± 3 | 32 ± 3 | 25 ± 4 | 40 ± 3* |
| CD8 (%) | 19 ± 3 | 21 ± 2 | 15 ± 2 | 22 ± 2* |
| CD4/CD8 | 1.81 ± 0.14 | 1.64 ± 0.17 | 2.09 ± 0.30 | 1.92 ± 0.17 |
| CD16 (%) | 6.7 ± 1.3 | 7.6 ± 1.3 | 6.2 ± 1.1 | 10.7 ± 2.1 |
| CD72 (%) | 3.6 ± 0.6 | 3.9 ± 0.6 | 4.1 ± 0.6 | 4.0 ± 0.5 |
| IgG (g/L) | 8.9 ± 0.5 | 9.7 ± 0.6 | 10.6 ± 1.5 | 9.7 ± 0.9 |
| IgA (g/L) | 3.5 ± 0.3 | 3.4 ± 0.3 | 2.4 ± 0.4 | 2.2 ± 0.1 |
| IgM (g/L) | 1.8 ± 0.2 | 1.8 ± 0.2 | 1.2 ± 0.2 | 1.2 ± 0.1 |
| Chemilumin luminol (spontaneous) | 877 ± 113 | 1360 ± 280 | 1008 ± 90 | 1427 ± 252* |
| Chemilumin luminol (induced) | 3451 ± 529 | 3174 ± 375 | 2943 ± 307 | 5063 ± 431* |
| Blast transformation spont | 477 ± 138 | 494 ± 149 | 435 ± 53 | 541 ± 48 |
| Blast transformation PHA | 5915 ± 1411 | 3552 ± 1212 | 4563 ± 524 | 8935 ± 780* |
| Adhesion (%) | 45 ± 8 | 50 ± 9 | 32 ± 3 | 41 ± 3* |
| NBT test spontaneous | 98 ± 11 | 84 ± 11 | 79 ± 12 | 77 ± 11 |
| NBT test induced | 148 ± 19 | 115 ± 15 | 111 ± 15 | 144 ± 17 |
| IL-1 production spontaneous | 496 ± 94 | 446 ± 132 | 481 ± 166 | 588 ± 201 |
| IL-1 production LPS induced | 731 ± 158 | 704 ± 217 | 1014 ± 157 | 1601 ± 284 |
| TNF production spontaneous | 160 ± 13 | 299 ± 83 | 134 ± 55 | 286 ± 27 |
| TNF prpoduction LPS induced | 215 ± 50 | 221 ± 14 | 370 ± 64 | 338 ± 81 |

*difference between paired group is statistically significant, $p < 0.005$ (Student 5 test)

TABLE 10

Bestim influence on biochemical and hematological parameters in surgical patients.

| | Placebo Before | Placebo After | Bestim Before | Bestim After |
|---|---|---|---|---|
| Total leukocytes (%) | 11 ± 1.4 | 11 ± 1.2 | 11 ± 1.2 | 8 ± 1.0* |
| Band neutrophils (%) | 13 ± 1.7 | 9 ± 1.7 | 12 ± 2 | 7 ± 1.6* |
| Mature neutrophils (%) | 77 ± 2 | 75 ± 2 | 76 ± 2 | 70 ± 1* |
| Monocytes (%) | 3.8 ± 0.9 | 3.1 ± 0.7 | 3.2 ± 0.5 | 3.6 ± 0.7* |
| Hemoglobin (g/L) | 98 ± 4 | 97 ± 6 | 98 ± 4 | 101 ± 4 |
| Plasma protein (g/L) | 63 ± 5 | 59 ± 2 | 70 ± 3 | 73 ± 3 |
| Albumin (g/L) | 33 ± 2 | 31 ± 2 | 38 ± 2 | 40 ± 2 |
| Bilirubin (µM/L) | 21 ± 8 | 21 ± 9 | 10 ± 1 | 7 ± 1 |
| Urea (mM/L) | 6.6 ± 1.1 | 6.7 ± 1.5 | 5.5 ± 0.3 | 4.0 ± 0.4* |
| Creatinin (µM/L) | 137 ± 23 | 160 ± 38 | 117 ± 7 | 98 ± 4 |
| Asparagine aminotransferase (IU/L) | 37 ± 5 | 39 ± 4 | 30 ± 9 | 17 ± 3* |
| Alanine aminotransferase (IU/L) | 28 ± 3 | 32 ± 3 | 29 ± 7 | 18 ± 3* |

Three cases of patient histories treated with Bestim are given below.

Case History 1: Immunodeficiency After Cancer Chemotherapy

Patient A, aged 44 years, was admitted with the diagnosis of colon cancer. Laboratory confirmed immunodeficiency which appeared as a complication of the main illness. Bestim preparation was applied by 5 daily intramuscular injections of 0.1 mg. Results are given in Table 11.

TABLE 11

Changes of leukocytes counts in the blood of patient with cancer-induced immunodeficiency after Bestim.

| Cell type and Cell Numbers | Before Therapy | After Bestim Therapy |
|---|---|---|
| White blood cells | $5.5 \times 10^3$ per $mm^3$ | $6.9 \times 10^3$ per $mm^3$ |
| Lymphocytes | 200 per $mm^3$ | 1800 per $mm^3$ |
| T-Lymphocytes (CD3) | 23% | 60% |
| T-helper lymphocytes (CD4) | 14% | 35% |

Case History 2: Bestim Treatment of Immunodeficiency Caused by Sepsis

Patient B, aged 70 years, was in the clinic with a diagnosis of sepsis. Immunodeficiency was confirmed by laboratory tests. Bestim was administered in the standard 5 daily intramuscular doses of 0.1 mg. Results are shown in Table 12.

TABLE 12

Changes in white blood cell counts in the blood of patient with sepsis after Bestim therapy.

| Cell type and Cell Numbers | Before Therapy | After Bestim Therapy |
|---|---|---|
| White blood cells | $10.2 \times 10^3$ per $mm^3$ | $9.8 \times 10^3$ per $mm^3$ |
| Lymphocytes | 560 per $mm^3$ | 1370 per $mm^3$ |
| T-Lymphocytes (CD3) | 23% | 75% |
| T-helper lymphocytes (CD4) | 11% | 50% |

Case History 3: Correction of Immunodeficiency Caused by Surgical Removal of the Thymus Patient C, aged 18 years, was in the clinic for immunodeficiency caused by surgical removal of the thymus gland. Bestim was administered in the standard 5 daily intramuscular dose of 0.1 mg. Results are given in Table 13.

TABLE 13

Leukocyte counts in blood of patient receiving Bestim after surgical removal of thymus gland.

| Cell type and Cell Numbers | Before Therapy | After Bestim Therapy |
|---|---|---|
| Lymphocytes | 1100 per $mm^3$ | 1980 per $mm^3$ |
| T-Lymphocytes (CD3) | 10% | 49% |

Other Studies in Humans

In addition to these studies, a trial was conducted using Bestim for the treatment of prostatitis caused by Chlamydian infection. Fourteen patients were treated with Bestim with 30 control patients. The results indicated that inflammation in the prostate was ameliorated by Bestim. Other clinical trials of efficacy in progress showed that use of Bestim ameliorates the signs and symptoms of viral hepatitis.

It is to be understood that while the invention has been described above in conjunction with preferred specific embodiments, the description and examples are intended to illustrate and not limit the scope of the invention, which is defined by the scope of the appended claims.

It is claimed:

1. The compound N-acetyl-γ-L-glutamyl-L-tryptophan.
2. The compound N-acetyl-γ-L-glutamyl-L-tryptophan.
3. The compound γ-L-glutamyl-$N_{in}$-formyl-L-tryptophan.
4. An immunomodulatory therapeutic method comprising:

administering to a patient a dose in the range of about 1 ng to about 1000 µg of body weight a compound selected from the group consisting of γ-L-glutamyl-L-tryptophan, N-methyl-γ-L-glutamyl-L-tryptophan, N-acetyl-γ-L-glutamyl-L-tryptophan, and γ-L-glutamyl-$N_{in}$-formyl-L-tryptophan.

5. The method as in claim 4 wherein the administration is as a single dose or a plurality of doses given intermittently.

6. The method as in claim 5 wherein the administration is by parenteral injection, oral or nasal inhalation, or oral ingestion.

7. The method as in claim 4 wherein the dose administered is an adjuvant to vaccination.

8. A therapeutic method for modulating a patient's immune system, comprising:

administering to the patient a compound having the structure:

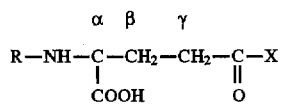

wherein R is hydrogen, acyl or alkyl, and X is a D- or L-heterocyclic amino acid or a heterocyclic derivative of a D- or L-amino acid, in an amount effective to modulate a patient's immune system.

9. The therapeutic method as in claim 8 wherein the compound administered is γ-L-glutamyl-L-tryptophan.

10. The therapeutic method as in claim 8 wherein the compound administered is N-methyl-γ-L-glutamyl-L-tryptophan.

11. The therapeutic method as in claim 8 wherein the compound administered is N-acetyl-γ-L-glutamyl-L-tryptophan.

12. The therapeutic method as in claim 8 wherein the compound administered is γ-L-glutamyl-$N_{in}$-formyl-L-tryptophan.

13. The therapeutic method as in claim 8 wherein the effective amount modulates the T upper cell population.

14. The therapeutic method as in claim 9 wherein the compound administered induces dose-dependent T-lymphocyte differentiation.

* * * * *